United States Patent
Eda et al.

(10) Patent No.: US 12,016,986 B2
(45) Date of Patent: Jun. 25, 2024

(54) BLOOD PURIFICATION APPARATUS USING PERISTALTIC PUMPS TO CIRCULATE A LIQUID FOR BLOOD TREATMENT

(71) Applicant: Nikkiso Company Limited, Tokyo (JP)

(72) Inventors: Yuki Eda, Shizuoka (JP); Masaaki Ohta, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 402 days.

(21) Appl. No.: 17/355,085

(22) Filed: Jun. 22, 2021

(65) Prior Publication Data

US 2021/0316050 A1 Oct. 14, 2021

Related U.S. Application Data

(63) Continuation of application No. PCT/JP2019/051340, filed on Dec. 26, 2019.

(30) Foreign Application Priority Data

Dec. 27, 2018 (JP) ................................ 2018-246177

(51) Int. Cl.
*A61M 1/16* (2006.01)
*A61M 60/113* (2021.01)
(Continued)

(52) U.S. Cl.
CPC ........ *A61M 1/1601* (2014.02); *A61M 60/113* (2021.01); *A61M 60/279* (2021.01);
(Continued)

(58) Field of Classification Search
CPC .............. A61M 1/1601; A61M 60/113; A61M 60/279; A61M 60/37; A61M 60/462;
(Continued)

(56) References Cited

U.S. PATENT DOCUMENTS 5,634,907 A * 6/1997 Rani ..................... A61M 5/142
604/153
2017/0028117 A1 * 2/2017 Mochizuki ........ A61M 5/14232

FOREIGN PATENT DOCUMENTS

EP 2682608 A1 1/2014
JP S60-148069 U 10/1985
(Continued)

OTHER PUBLICATIONS

European Search Report for Application No. 19902995.0, dated Jul. 18, 2022, 7 pgs.
(Continued)

*Primary Examiner* — Hayden Brewster

(74) *Attorney, Agent, or Firm* — Young Basile Hanlon & MacFarlane, P.C.

(57) ABSTRACT

A blood purification apparatus includes: a peristaltic pump that includes a stator to which a pump tube including a first portion and a second portion is detachably attached, and a rotor including a roller and a guide portion, the roller delivering liquid by squeezing the pump tube, the guide portion retaining the pump tube so that the pump tube is squeezable with the roller about a predetermined axis; an anchor member that anchors an attaching member to which the pump tube is attached; and a displacing portion that displaces the attaching member between a set position and an unset position by moving the anchor member with the attaching member being anchored by the anchor member.

18 Claims, 14 Drawing Sheets

(51) Int. Cl.
*A61M 60/279* (2021.01)
*A61M 60/37* (2021.01)
*A61M 60/462* (2021.01)

(52) U.S. Cl.
CPC .......... *A61M 60/37* (2021.01); *A61M 60/462* (2021.01); *A61M 2205/14* (2013.01)

(58) Field of Classification Search
CPC ............ A61M 2205/14; A61M 60/835; A61M 2205/6018; A61M 1/367
See application file for complete search history.

(56) References Cited

FOREIGN PATENT DOCUMENTS

| JP | H11504836 A | 5/1999 |
|---|---|---|
| JP | 3452073 B2 | 9/2003 |
| JP | 2005-074234 A | 3/2005 |
| JP | 2006-212050 A | 8/2006 |
| JP | 2008-000425 A | 1/2008 |
| JP | 2010-190062 A | 9/2010 |
| JP | 2015-073847 A | 4/2015 |
| JP | 2015-202248 A | 11/2015 |
| JP | 2017-140521 A | 8/2017 |
| JP | 2017-164285 A | 9/2017 |
| WO | 1995/017603 A1 | 6/1995 |
| WO | 1996/040322 A2 | 12/1996 |
| WO | 2013/090579 A1 | 6/2013 |
| WO | 2013/098028 A1 | 7/2013 |
| WO | 2015/159915 A1 | 10/2015 |
| WO | 2018/225027 A1 | 12/2018 |

OTHER PUBLICATIONS

Potentially related to U.S. Appl. No. 17/347,852, filed Jun. 15, 2021, and previsouly published as WO2020/137016 A1.
Potentially related to U.S. Appl. No. 17/348,037, filed Jun. 15, 2021, and previously published as WO2020/138380 A1.
Potentially related to U.S. Appl. No. 17/348,051, filed Jun. 15, 2021, and previosuly published as WO2020/138381 A1.
Potentially related to U.S. Appl. No. 17/350,408, filed Jun. 17, 2021, and previously published as WO2020/138382 A1.
Potentially related to U.S. Appl. No. 17/350,414, filed Jun. 17, 2021, and previsouly published as WO2020/138383 A1.

* cited by examiner

[Fig. 1]
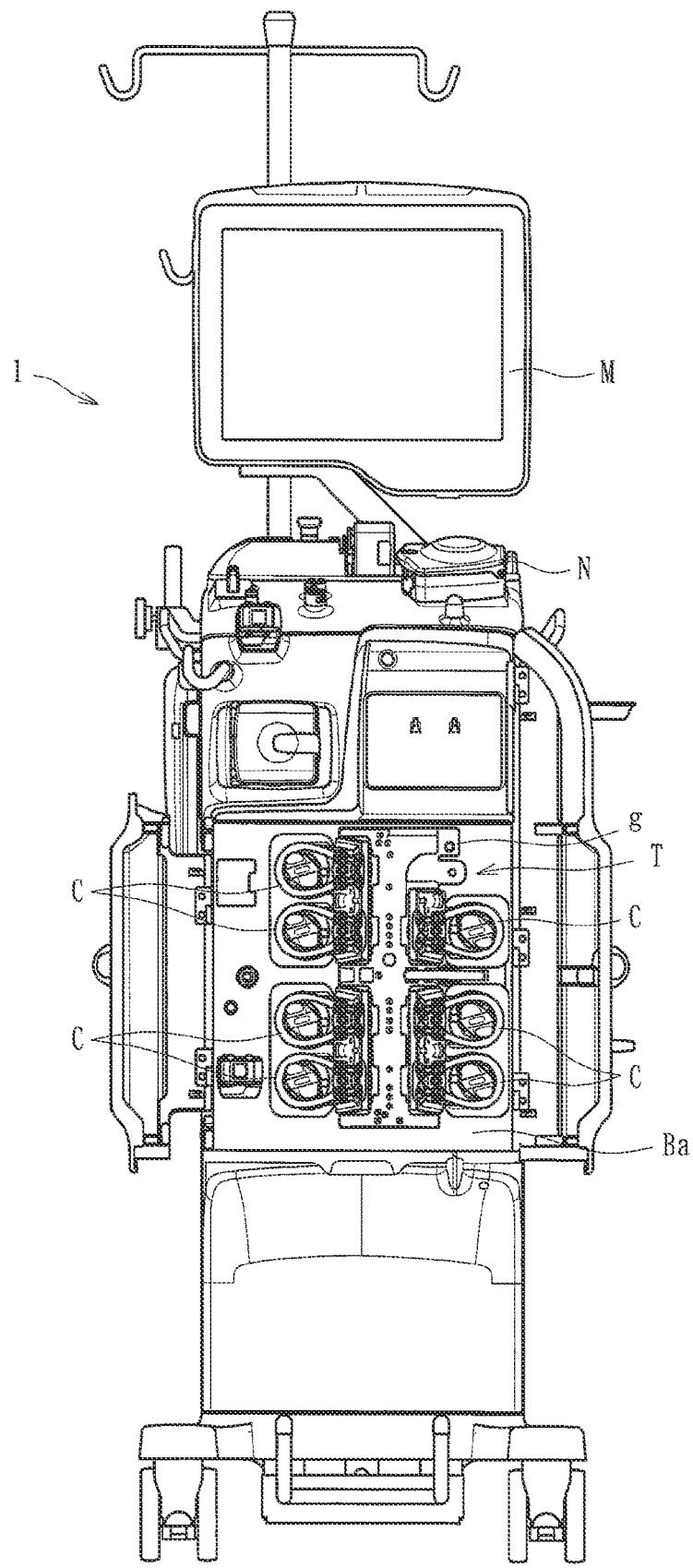

[Fig. 2]
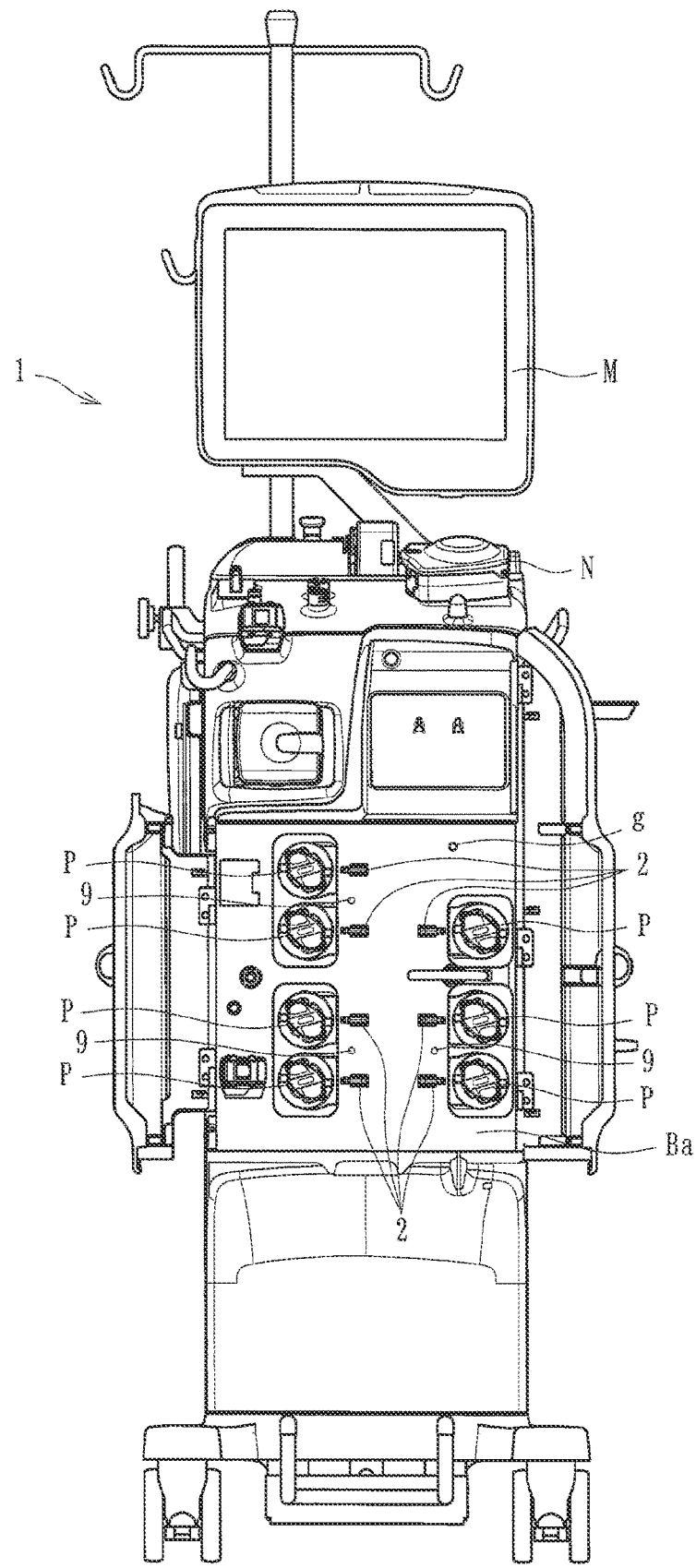

[Fig. 3]
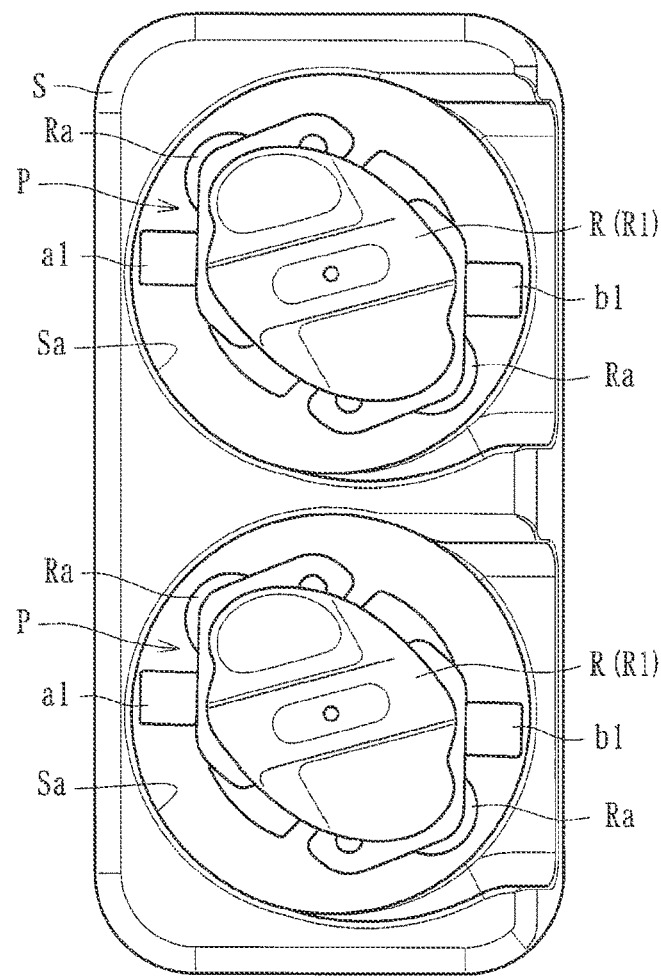
[Fig. 4]
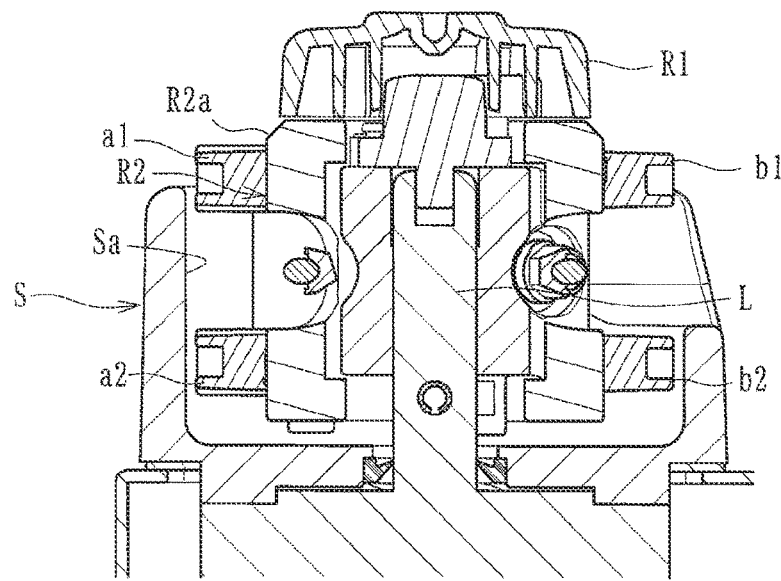

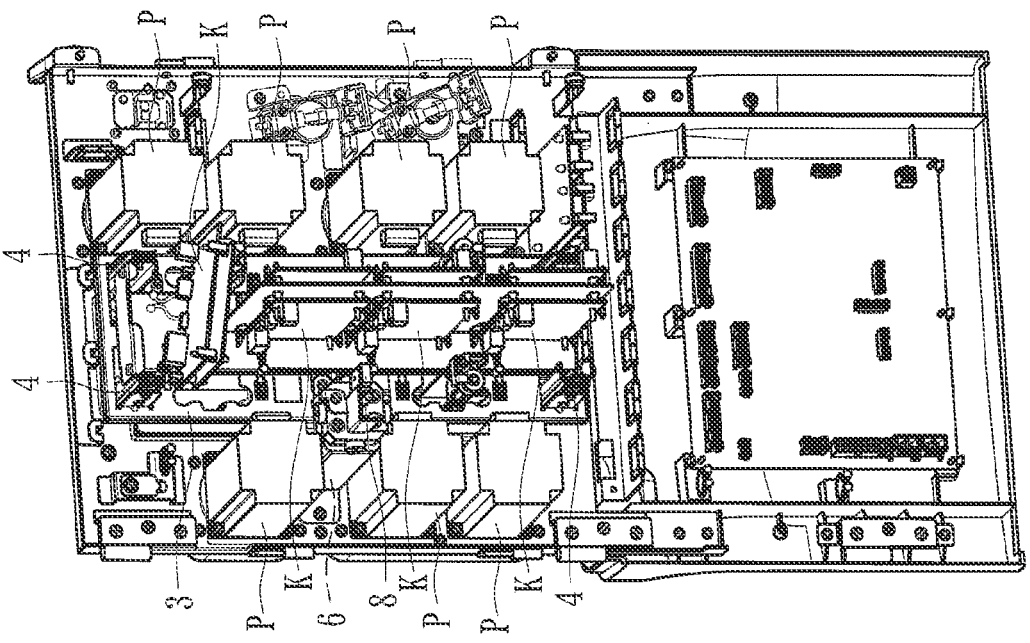
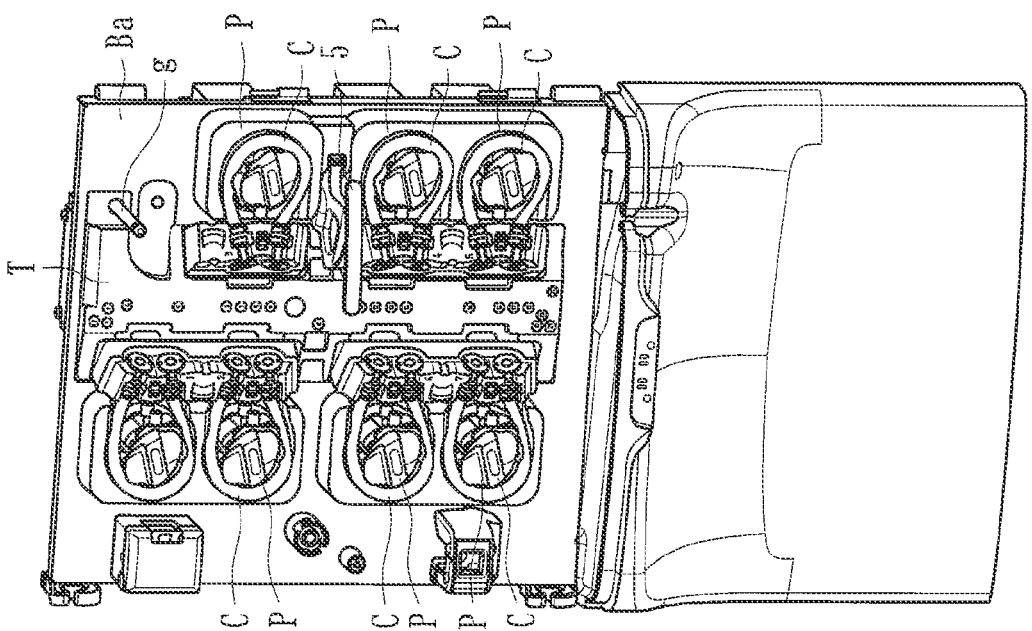

[Fig. 6]
(a)
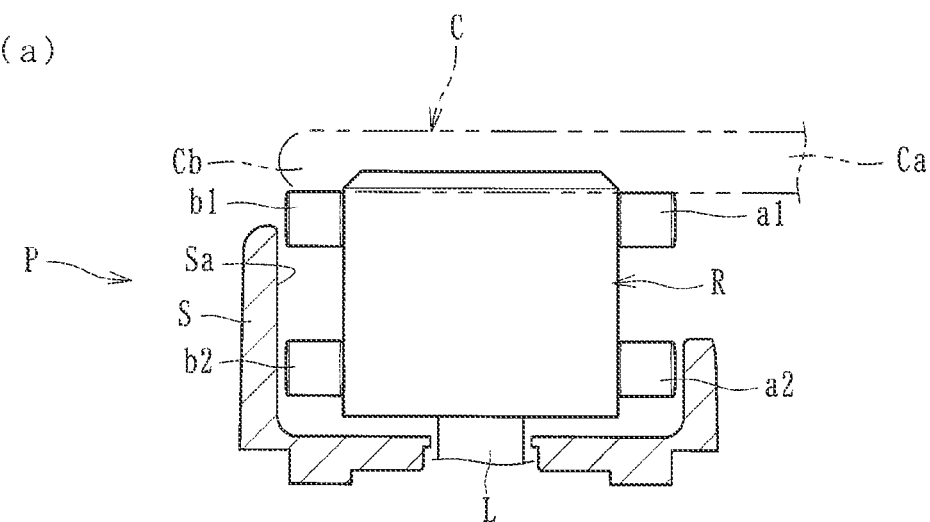
(b)
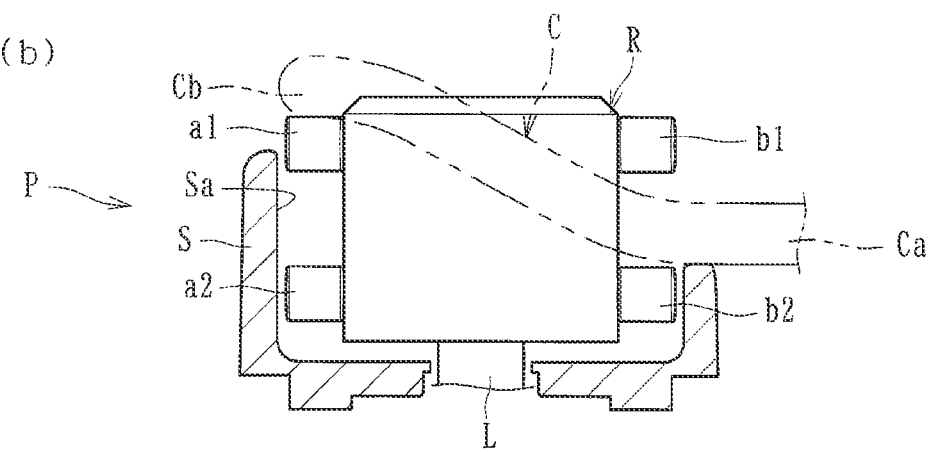
(c)
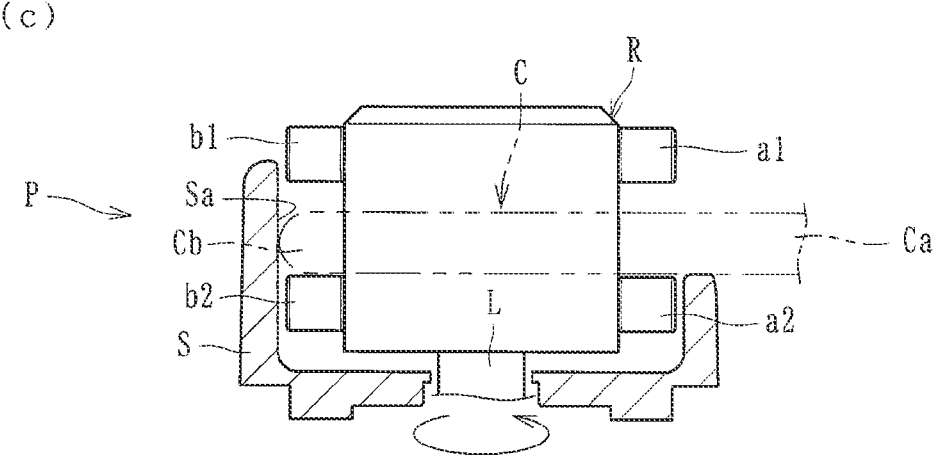

[Fig. 7]
(a)
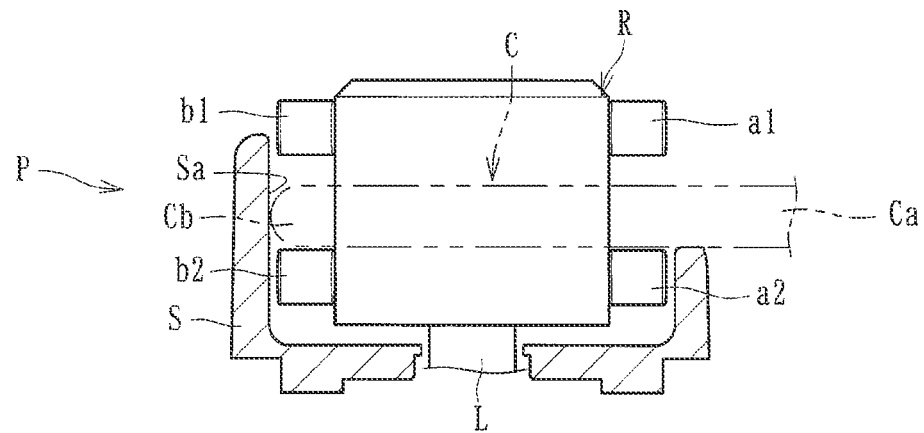
(b)
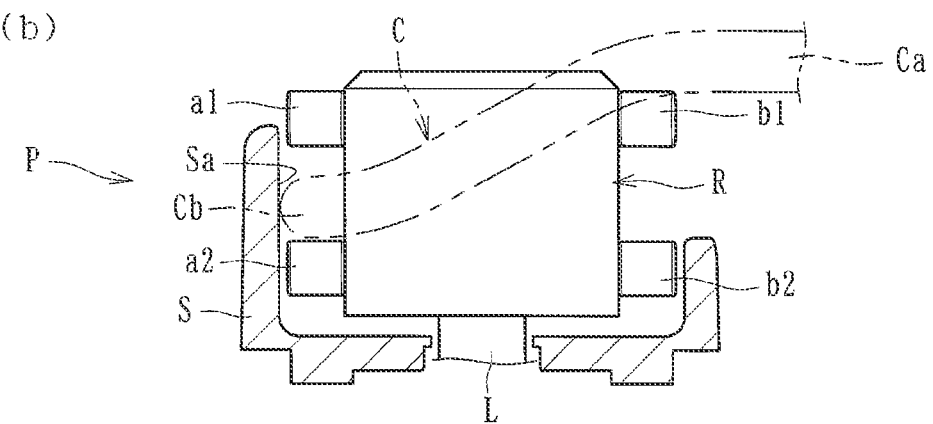
(c)
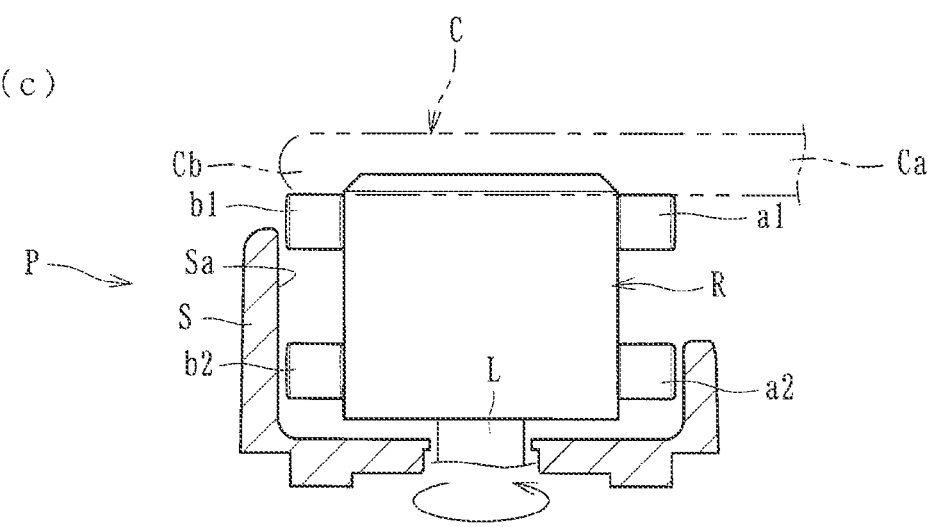

[Fig. 8]
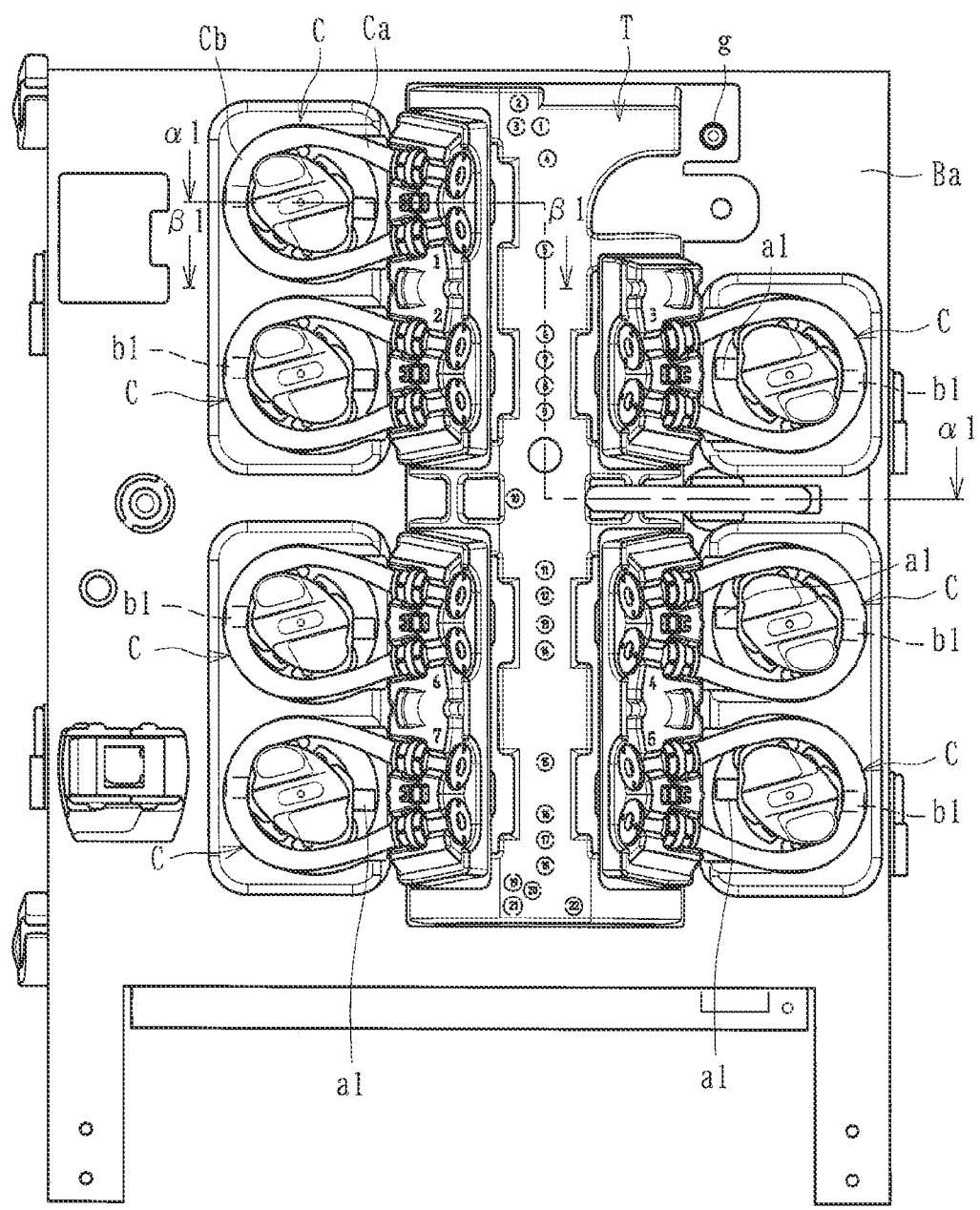

[Fig. 9]
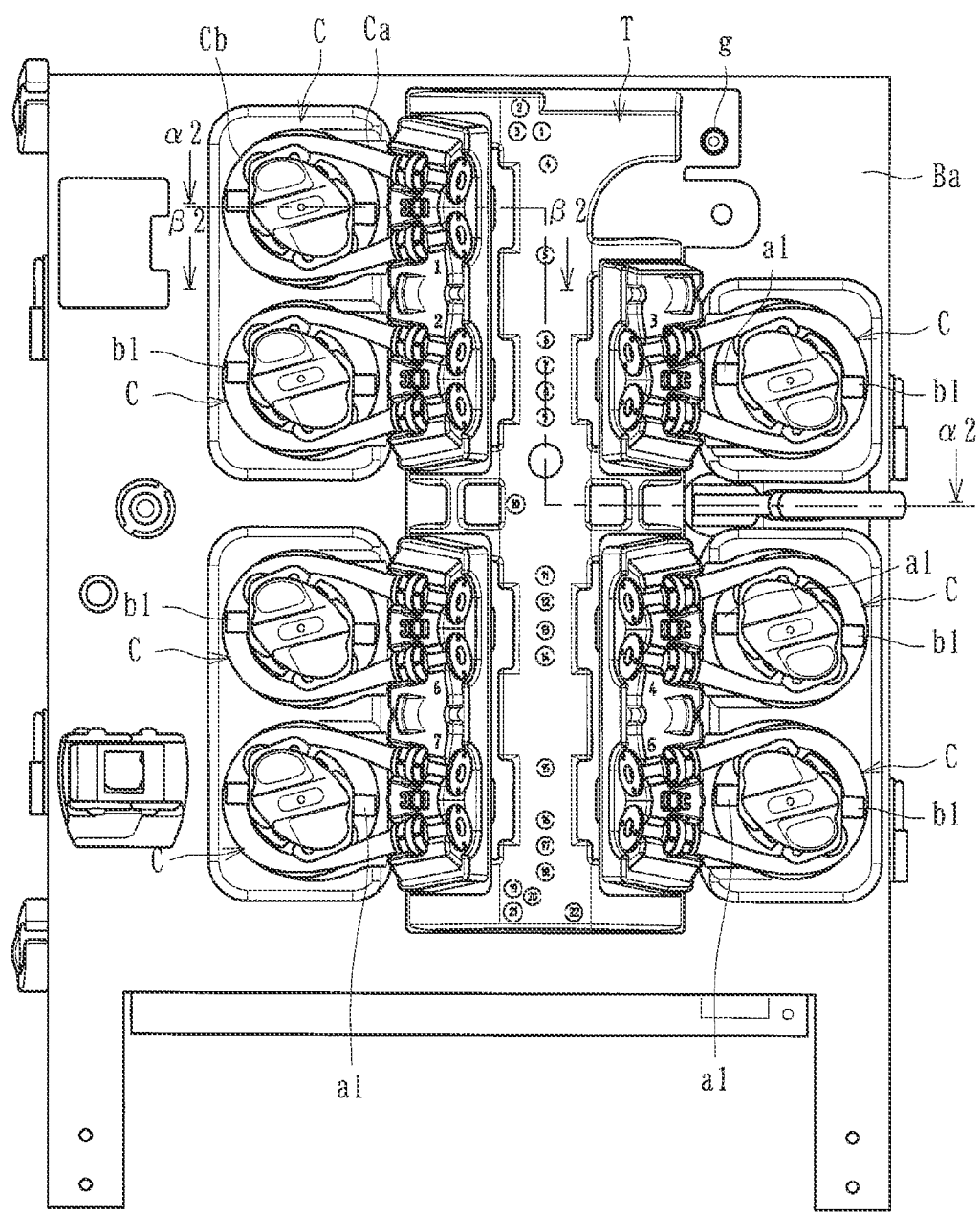

[Fig. 10]
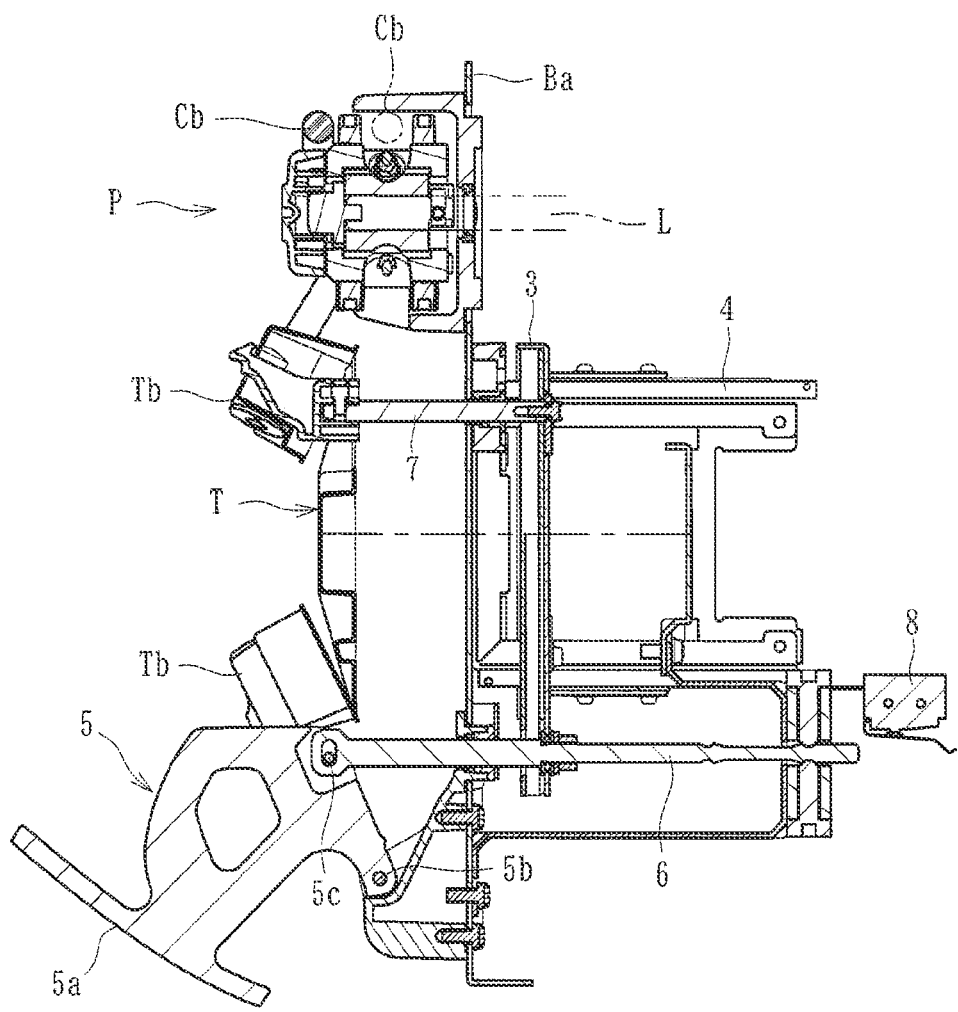

[Fig. 11]
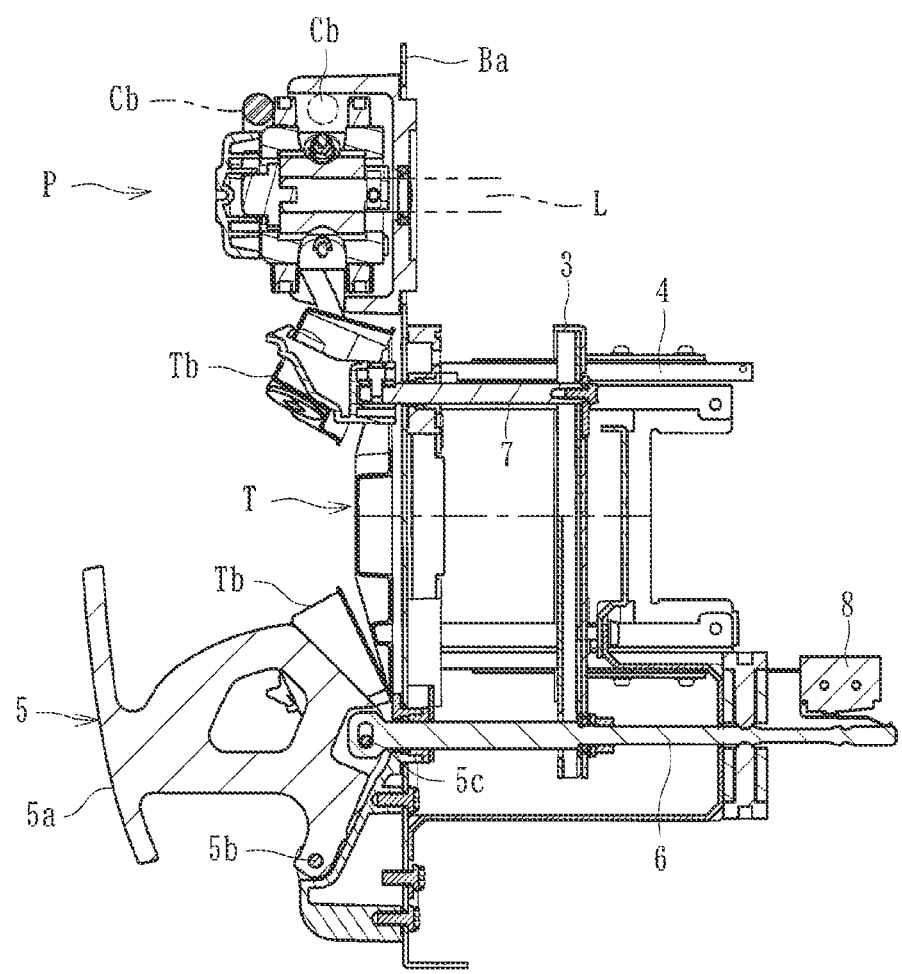

[Fig. 12]
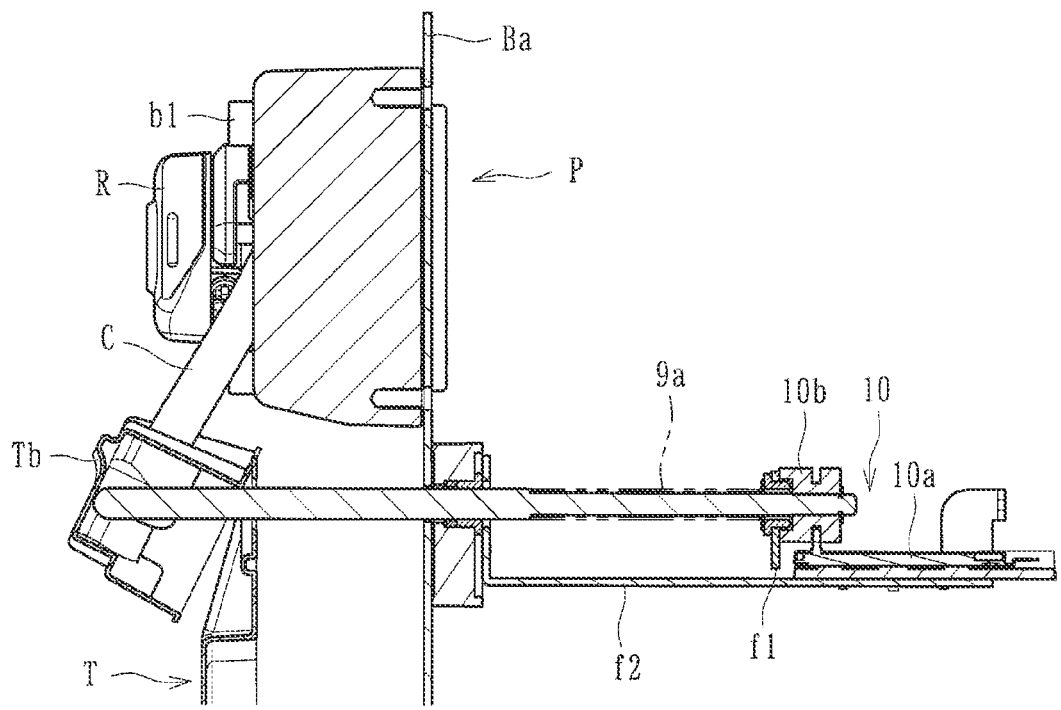
[Fig. 13]
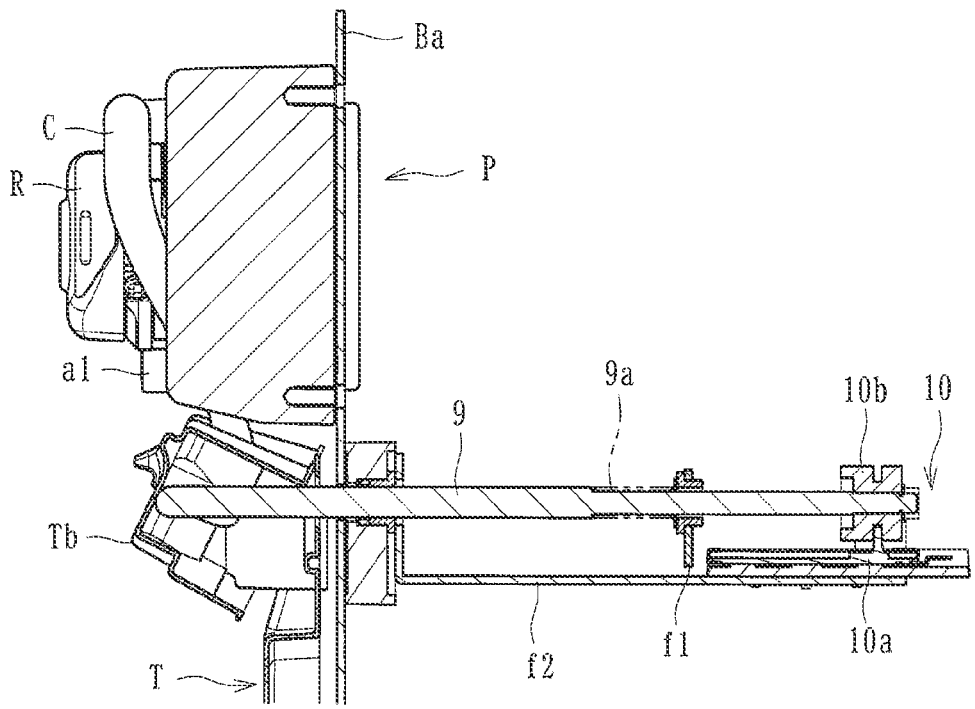

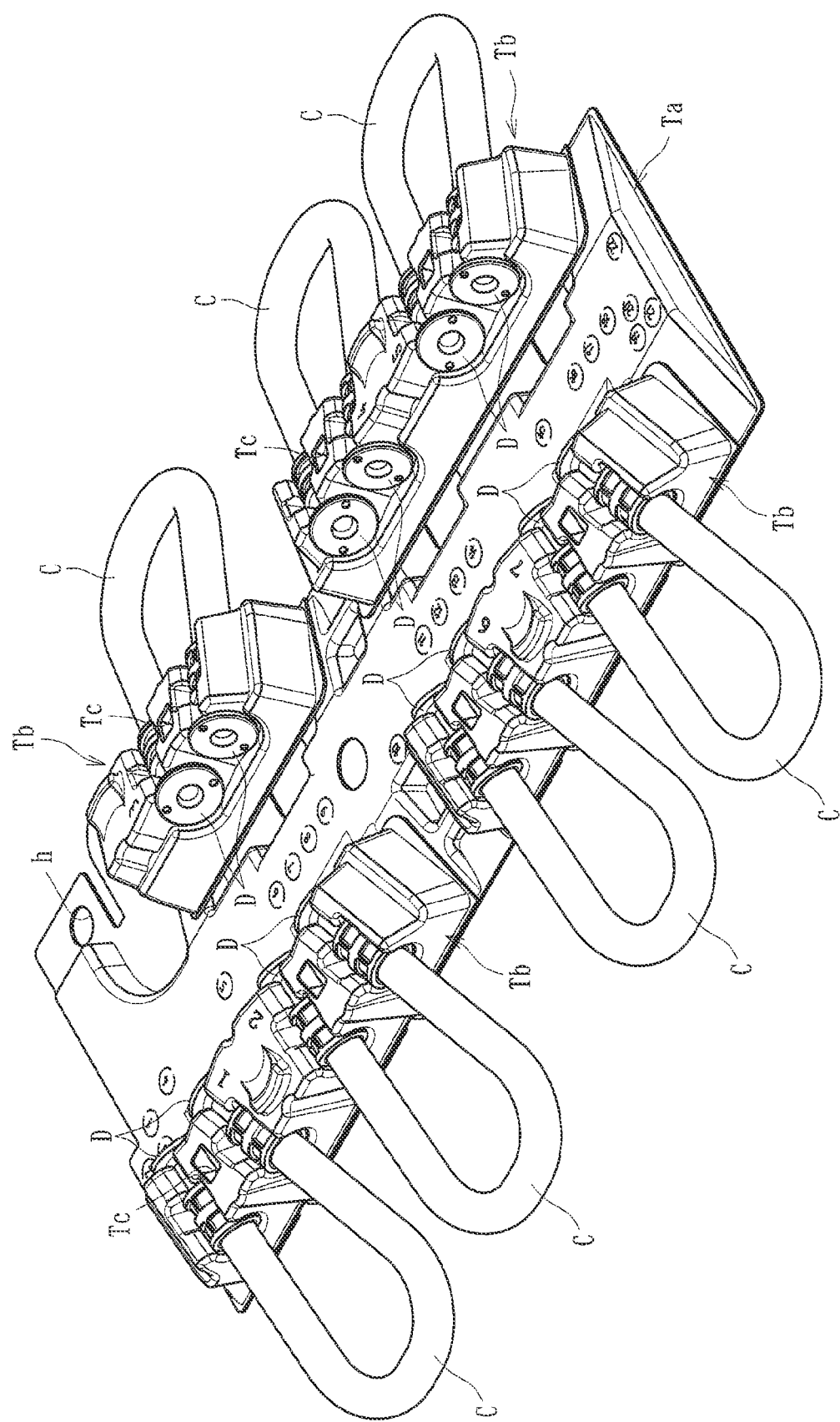

[Fig. 15]
(a)
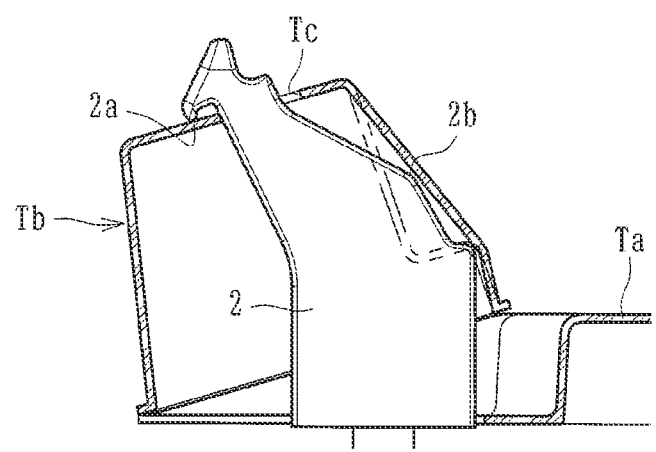
(b)
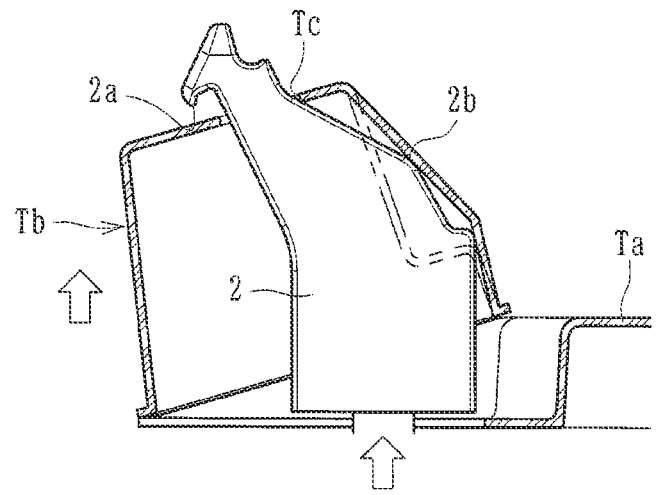

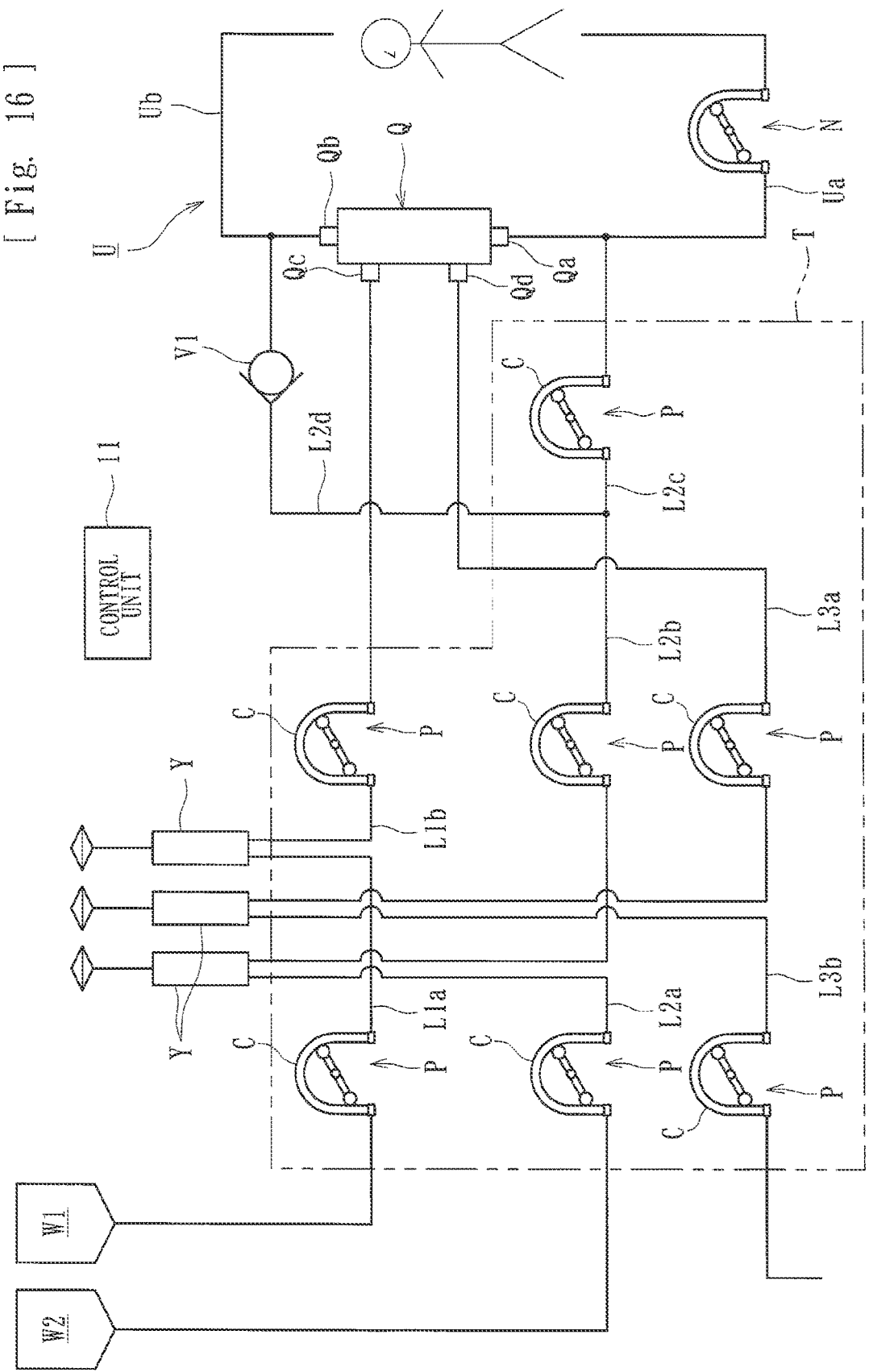

BLOOD PURIFICATION APPARATUS USING PERISTALTIC PUMPS TO CIRCULATE A LIQUID FOR BLOOD TREATMENT

CROSS-REFERENCE TO RELATED APPLICATION(S)

This application is a continuation of International Application No. PCT/JP2019/051340 filed on Dec. 26, 2019, which claims priority to Japanese Application No. 2018-246177, filed on Dec. 27, 2018, the entire disclosures of which are hereby incorporated by reference.

FIELD

The present teachings relate to a blood purification apparatus including a peristaltic pump.

BACKGROUND

In general, a blood purification apparatus for giving dialysis treatment is provided with an arterial blood circuit and a venous blood circuit that form a blood circuit for causing blood of a patient to extracorporeally circulate, a blood purifier for purifying the blood extracorporeally circulating through the blood circuit, and various treatment devices, such as a blood pump, for performing blood purification treatment with the blood circuit and the blood purifier. After the patient is punctured with an arterial puncture needle and a venous puncture needle, the blood pump is activated. Thus, blood of the patient flows through the arterial blood circuit and the venous blood circuit. In such a flowing process, the blood is purified by the blood purifier.

Some of blood purification apparatuses according to known proposals each include a plurality of peristaltic pumps for delivering liquids such as substitution fluid and drain liquid. The peristaltic pumps are provided with pump tubes, respectively, so that different liquids can be delivered. Hitherto, for example, an attaching member has been disclosed by PTL 1 that includes a plurality of pump tubes attachable to respective peristaltic pumps included in a blood purification apparatus. The attaching member is to be attached to a predetermined position of the blood purification apparatus.

PTL 1: Japanese Unexamined Patent Application Publication No. 2015-73847 the teachings of which is expressly incorporated by reference herein for all purposes.

SUMMARY

In the above known blood purification apparatus, however, to attach the pump tubes to the peristaltic pumps, a worker needs to insert the pump tubes into respective stators while rotating respective rotors. Such attaching work is troublesome. Furthermore, to detach the pump tubes from the peristaltic pumps, the worker needs to remove the pump tubes from the stators while rotating the rotors. Such detaching work is also troublesome.

The present teachings have been conceived in view of the above circumstances and provides a blood purification apparatus in which the work of attaching or detaching a pump tube to or from a peristaltic pump can be performed with increased ease.

According to variation 1, there is provided a blood purification apparatus including the following: a peristaltic pump that includes a stator to which a pump tube including a first portion and a second portion is detachably attached, and a rotor including a roller and a guide portion, the roller delivering liquid by squeezing the pump tube attached to the stator, the guide portion retaining the pump tube at an appropriate position where the pump tube is squeezable with the roller, the rotor being rotatable about a predetermined axis; an anchor member that anchors an attaching member to which the pump tube is attached; and a displacing portion that displaces the attaching member between a set position and an unset position by moving the anchor member with the attaching member being anchored by the anchor member. An attachable state in which the first portion of the pump tube rests at the appropriate position is established when the anchor member is moved from the unset position to the set position with the guide portion of the peristaltic pump being stopped in a specific phase. Loading in which the guide portion draws the pump tube into the stator such that the first portion and the second portion of the pump tube rest at the appropriate position is executed when the peristaltic pump is activated in the attachable state such that the rotor is rotated by a predetermined angle.

According to variation 2, there is provided a blood purification apparatus including the following: a peristaltic pump that includes a rotor, the rotor including a roller and a guide portion, the roller delivering liquid by squeezing a pump tube attached to a stator, the guide portion retaining the pump tube at an appropriate position where the pump tube is squeezable with the roller; an anchor member that anchors an attaching member to which the pump tube is attached; and a displacing portion that displaces the attaching member between a set position and an unset position by moving the anchor member with the attaching member being anchored by the anchor member. A detachable state in which a first portion of the pump tube rests at an inappropriate position deviating from the appropriate position is established when the anchor member is moved from the set position to the unset position with the guide portion of the peristaltic pump being stopped in a specific phase. Unloading in which the guide portion pushes the pump tube out of the stator such that the first portion and a second portion of the pump tube rest at the inappropriate position is executed when the peristaltic pump is activated in the detachable state such that the rotor is rotated by a predetermined angle.

According to variation 3, the blood purification apparatus according to variation 1 or 2 further includes a control unit that stops the rotor with the guide portion being in the specific phase and executes the loading or unloading by rotating the rotor by the predetermined angle.

According to variation 4, in the blood purification apparatus according to any of variations 1 to 3, the peristaltic pump is one of a plurality of peristaltic pumps, the pump tube is one of a plurality of pump tubes attached to the attaching member, a number of the plurality of pump tubes is equal to a number of the plurality of peristaltic pumps, and the plurality of pump tubes are loaded or unloaded by moving the anchor member between the set position and the unset position.

According to variation 5, the blood purification apparatus according to any of variations 1 to 4 further includes an operating portion with which the displacing portion is operated in such a manner as to displace the attaching member between the set position and the unset position by moving the anchor member. Furthermore, the operating portion has an assisting function of assisting exertion of an operating force.

According to variation 6, the blood purification apparatus according to any of variations 1 to 5 further includes a detecting unit that detects establishment of the attachable state or detachable state of the pump tube.

According to variation 7, in the blood purification apparatus according to variation 6, the pump tube is one of a plurality of pump tubes attached to the attaching member, a number of the plurality of pump tubes is equal to a number of the plurality of peristaltic pumps, and the detecting unit detects any of the pump tubes that has failed to be in the attachable state or detachable state and identifies one of the peristaltic pumps that corresponds to the detected pump tube.

According to variation 8, in the blood purification apparatus according to variation 7, the detecting unit detects establishment of the attachable state or detachable state of the pump tubes to be loaded onto or unloaded from adjacent ones of the peristaltic pumps.

According to variation 1, the attachable state in which the first portion of the pump tube rests at the appropriate position is established when the anchor member is moved from the unset position to the set position with the guide portion of the peristaltic pump being stopped in the specific phase. Furthermore, loading in which the guide portion draws the pump tube into the stator such that the first portion and the second portion of the pump tube rest at the appropriate position is executed when the peristaltic pump is activated in the attachable state such that the rotor is rotated by the predetermined angle. Therefore, the ease of work in attaching the pump tube to the peristaltic pump can be increased.

According to variation 2, the detachable state in which the first portion of the pump tube rests at the inappropriate position deviating from the appropriate position is established when the anchor member is moved from the set position to the unset position with the guide portion of the peristaltic pump being stopped in the specific phase. Furthermore, unloading in which the guide portion pushes the pump tube out of the stator such that the first portion and the second portion of the pump tube rest at the inappropriate position is executed when the peristaltic pump is activated in the detachable state such that the rotor is rotated by the predetermined angle. Therefore, the ease of work in detaching the pump tube from the peristaltic pump can be increased.

According to variation 3, the blood purification apparatus further includes the control unit that stops the rotor with the guide portion being in the specific phase and executes the loading or unloading by rotating the rotor by the predetermined angle. Therefore, the ease of work in attaching or detaching the pump tube to or from the peristaltic pump can be increased further.

According to variation 4, the peristaltic pump is one of a plurality of peristaltic pumps, the pump tube is one of a plurality of pump tubes attached to the attaching member, a number of the plurality of pump tubes is equal to a number of the plurality of peristaltic pumps, and the plurality of pump tubes are loaded or unloaded by moving the anchor member between the set position and the unset position. Therefore, the plurality of pump tubes can be loaded or unloaded at a time. Consequently, work hours can be reduced.

According to variation 5, the blood purification apparatus further includes the operating portion with which the displacing portion is operated in such a manner as to displace the attaching member between the set position and the unset position by moving the anchor member. Furthermore, the operating portion has an assisting function of assisting exertion of an operating force. Therefore, the ease of operation of the operating portion can be increased. Consequently, the movement of the anchor member and the displacement of the attaching member can be achieved smoothly.

According to variation 6, the blood purification apparatus further includes the detecting unit that detects the establishment of the attachable state or detachable state of the pump tube. Therefore, a situation where loading or unloading is not completed appropriately can be recognized.

According to variation 7, the pump tube is one of a plurality of pump tubes attached to the attaching member, and the number of the plurality of pump tubes is equal to the number of the plurality of peristaltic pumps. Furthermore, the detecting unit detects any of the pump tubes that has failed to be in the attachable state or detachable state and identifies one of the peristaltic pumps that corresponds to the detected pump tube. Therefore, in which of the plurality of peristaltic pumps the situation where loading or unloading is not completed appropriately is occurring can be recognized.

According to variation 8, the detecting unit detects the establishment of the attachable state or detachable state of the pump tubes to be loaded onto or unloaded from adjacent ones of the peristaltic pumps. Therefore, the number of detecting units required can be reduced. Consequently, the manufacturing cost can be reduced.

BRIEF DESCRIPTION

FIG. 1 is an overall diagram of a blood purification apparatus according to an embodiment of the present invention (with an attaching member attached thereto).

FIG. 2 is an overall diagram of the blood purification apparatus, with the attaching member yet to be attached thereto.

FIG. 3 is an enlargement of peristaltic pumps included in the blood purification apparatus.

FIG. 4 is a sectional view of the peristaltic pump included in the blood purification apparatus, illustrating an internal configuration thereof.

FIG. 5 illustrates a member of the blood purification apparatus to which the attaching member is attached, and includes (a) a front perspective view and (b) a rear perspective view.

FIG. 6 illustrates a process of attaching a pump tube to the peristaltic pump of the blood purification apparatus, including diagram (a) illustrating a state before an anchor member is moved, diagram (b) illustrating a state after the anchor member is moved but before loading is complete, and diagram (c) illustrating a state after loading is complete.

FIG. 7 illustrates a process of detaching the pump tube from the peristaltic pump of the blood purification apparatus, including diagram (a) illustrating a state before the anchor member is moved, diagram (b) illustrating a state after the anchor member is moved but before unloading is complete, and diagram (c) illustrating a state after unloading is complete.

FIG. 8 is a schematic diagram of the attaching member that is at an unset position in the blood purification apparatus.

FIG. 9 is a schematic diagram of the attaching member that is at a set position in the blood purification apparatus.

FIG. 10 is a sectional view taken along line $\alpha 1$-$\alpha 1$ illustrated in FIG. 8.

FIG. 11 is a sectional view taken along line $\alpha 2$-$\alpha 2$ illustrated in FIG. 9.

FIG. 12 is a sectional view taken along line $\beta 1$-$\beta 1$ illustrated in FIG. 8.

FIG. 13 is a sectional view taken along line β2-β2 illustrated in FIG. 8.

FIG. 14 is a perspective view of the attaching member to be attached to the blood purification apparatus.

FIG. 15 includes schematic diagrams of the anchor member included in the blood purification apparatus, illustrating (a) a state where the attaching member is anchored and (b) a state where the anchor member is displaced from the set position to the unset position.

FIG. 16 is a diagram of the blood purification apparatus with the attaching member attached thereto, and is provided for describing blood purification treatment.

DETAILED DESCRIPTION

Embodiments of the present invention will now be described specifically with reference to the drawings.

As illustrated in FIGS. 1 and 2, a blood purification apparatus 1 according to the present embodiment is a monitoring apparatus for hemodialysis treatment that includes a monitor M capable of displaying information regarding blood purification treatment and the like, a blood pump N, and so forth. When the blood pump N is activated, blood of a patient is caused to extracorporeally circulate through a blood circuit. Meanwhile, the blood undergoes blood purification treatment in a blood purifier (a dialyzer Q). The blood purification apparatus 1 according to the present embodiment includes a plurality of (seven in the present embodiment) peristaltic pumps P provided on the front face thereof, so that substitution fluid and drain liquid can be delivered in the blood purification treatment.

As illustrated in FIGS. 1 and 5, the blood purification apparatus 1 according to the present embodiment is provided with an attaching member T to be attached thereto. The attaching member T holds pump tubes C to be squeezed in a predetermined direction by the respective peristaltic pumps P for liquid delivery. As illustrated in FIG. 14, the attaching member T includes a body Ta attachable to a predetermined position Ba of the blood purification apparatus 1, and holding portions Tb attached to the body Ta and that hold the pump tubes C.

The attaching member T is a resin molded component in which the body Ta and the holding portions Tb are formed continuously with each other. When the component is folded at folds extending along the boundaries between the body Ta and the holding portions Tb, the holding portions Tb are placed on the front face of the body Ta in such a manner as to project therefrom. The folds each have perforations or the like. Therefore, the holding portions Tb are easily foldable with respect to the body Ta.

The holding portions Tb are each a resin molded part projecting in a block-like shape from the body Ta (projecting frontward). The holding portions Tb have holding grooves, into each of which one of connectors D provided at two respective ends of each of the pump tubes C is to be fitted, whereby the connectors D are securable at a predetermined height. In short, the connectors D are secured by being fitted into the holding grooves, whereby the pump tubes C are held by the holding portions Tb as illustrated in FIG. 14. Furthermore, as illustrated in the same drawing, the holding portions Tb have anchoring holes Tc in predetermined areas thereof and are therefore anchorable by anchor members 2 included in the blood purification apparatus 1.

The pump tubes C are each made of a material such as soft resin or rubber forming a flow route with a relatively large diameter. Each pump tube C has a loop shape including proximal portions Ca (first portions) and a distal portion Cb (a second portion). The connectors D are provided at the proximal portions Ca, respectively. After the pump tubes C are each attached to a predetermined position (an appropriate position where the pump tube C is squeezable by rollers Ra) in a corresponding one of stators S of the peristaltic pumps P, respective rotors R are driven to rotate. Thus, the pump tubes C are squeezed in the lengthwise direction by the rollers Ra, so that liquids such as substitution fluid and drain liquid can be delivered.

The holding portions Tb according to the present embodiment are provided on inclined surfaces of the body Ta. Therefore, the pump tubes C each extend at a predetermined angle (inclined along the inclined surface) with respect to the bottom surface of the body Ta (the attaching surface that faces the predetermined position Ba). In other words, the holding portions Tb according to the present embodiment hold the connectors D of the pump tubes C in an inclined state. Specifically, the holding portions Tb hold the pump tubes C such that the pump tubes C are inclined in a direction in which the pump tubes C are attached to the peristaltic pumps P.

The body Ta according to the present embodiment is configured such that tubes (not illustrated) forming liquid flow routes connected to the connectors D of the pump tubes C are placed in a central portion thereof. Specifically, the central portion of the body Ta according to the present embodiment has a concavity that is open on the rear side, and the tubes connected to the connectors D of the pump tubes C are placed along the concavity.

The peristaltic pumps P are each capable of delivering liquid by squeezing the pump tube C in a specific direction and each include, as illustrated in FIGS. 3 and 4, the stator S having a fitting recess Sa, the rotor R provided in the fitting recess Sa and being rotatable about a rotating shaft L (a virtual axis of rotation that passes through the rotating shaft L), and the rollers Ra and guide pins (upper guide pins a1 and b1 and lower guide pins a2 and b2) (guide portions) provided on the rotor R. When the pump tube C is fitted into the fitting recess Sa of the stator S and the rotor R is driven to rotate about the predetermined axis, the pump tube C is squeezed between the wall of the fitting recess Sa and the rollers Ra. Thus, the liquid can be delivered.

The rotor R has the upper guide pin a1 and the lower guide pin a2 provided in a pair, and the upper guide pin b1 and the lower guide pin b2 provided in a pair, all of which project from the rotor R. The pump tube C is to be fitted between the upper guide pin a1 and the lower guide pin a2 and between the upper guide pin b1 and the lower guide pin b2. The upper guide pins a1 and b1 are positioned on the open side of the fitting recess Sa. The lower guide pins a2 and b2 are positioned on the bottom side of the fitting recess Sa. Thus, the pump tube C fitted in the fitting recess Sa of the stator S is held at the appropriate position (the appropriate position where the pump tube C is squeezable by the rollers Ra), and displacement of the pump tube C from the appropriate position is suppressed.

The blood purification apparatus 1 according to the present embodiment receives the attaching member T attachable to the predetermined position Ba on the front face thereof, where the peristaltic pumps P are provided. Specifically, as illustrated in FIGS. 1 and 2, the blood purification apparatus 1 according to the present embodiment has a positioning pin g. When the positioning pin g is inserted into a positioning hole h provided in the body Ta of the attaching member T, the attaching member T can be positioned at the predetermined position Ba of the blood purification apparatus 1.

As illustrated in FIG. 2, the blood purification apparatus 1 according to the present embodiment further has a plurality of (seven in the present embodiment) anchor members 2 at the predetermined position Ba. Meanwhile, as described above, the holding portions Tb have the anchoring holes Tc at which the holding portions Tb are anchorable by the anchor members 2. As illustrated in FIG. 15, the anchor members 2 each include an anchor hook 2a on one side of the distal end thereof, and a pushing portion 2b on the other side. The anchor hook 2a is hooked on the peripheral edge of the anchoring hole Tc (see FIG. 15(a)). Thus, the attaching member T is anchored by the anchor member 2 and is secured to the predetermined position Ba.

A displacing portion 3 displaces the attaching member T between a set position (a position illustrated in FIGS. 8, 10, and 12) and an unset position (a position illustrated in FIGS. 9, 11, and 13) by moving the anchor members 2 with the attaching member T being anchored by the anchor members 2. The displacing portion 3 is movable while being guided by guiding portions 4. Specifically, as illustrated in FIG. 5(b), the guiding portions 4 are fixed to the back surface of a member where the predetermined position Ba is defined. The displacing portion 3, which has a frame shape and is fittable to the guiding portions 4, is slidably attached to the guiding portions 4.

As illustrated in FIGS. 10 and 11, an interlocking member 6 connected to an operating portion 5 and interlocking members 7 connected to the anchor members 2 are attached to the displacing portion 3. When the operating portion 5 is operated, the displacing portion 3 moves while being guided by the guiding portions 4 (moves in the lateral direction in the drawings). With this movement, the anchor members 2 can be moved. When the anchor hooks 2a are hooked on the attaching member T with the anchor members 2 being positioned apart from the predetermined position Ba, the attaching member T can rest at the unset position. Then, the displacing portion 3 is operated to slide in such a manner as to move the anchor members 2 to positions near the predetermined position Ba, whereby the attaching member T can rest at the set position.

As illustrated in FIGS. 10 and 11, the blood purification apparatus 1 according to the present embodiment further includes a detection switch 8 fixedly provided therein. When the operating portion 5 is operated, the interlocking member 6 moves. The detection switch 8 is capable of detecting the position of the interlocking member 6 thus operated. Therefore, the operation of the operating portion 5 is detectable. The guiding portions 4 according to the present embodiment are provided with control boards K that carry devices such as a control unit 11 (see FIG. 16) for controlling the operation of the peristaltic pumps P, and control circuits for controlling various operations.

As described above, the operating portion 5 is provided for operating the displacing portion 3 in such a manner as to displace the attaching member T between the set position and the unset position by moving the anchor members 2. The operating portion 5 has an assisting function of assisting the exertion of an operating force. Specifically, as illustrated in FIGS. 10 and 11, the operating portion 5 includes a grip part 5a gripped by an operator for operation, a rocking center 5b serving as a rocking axis of the operating portion 5, and a connecting part 5c connected to the interlocking member 6. When the grip part 5a is operated, the operating portion 5 rocks about the rocking center 5b. The operating portion 5 cooperating with the interlocking member 6 can thus move the displacing portion 3 and the anchor members 2 by leverage. The operating portion 5 has an assisting function (i.e., a so-called servo mechanism) exerted by using "leverage". The assisting function of assisting the exertion of an operating force may be another function provided as a link or the like.

In the blood purification apparatus 1 according to the present embodiment, when the attaching member T is positioned by the positioning pin g and is anchored at the anchoring holes Tc by the anchor hooks 2a of the anchor members 2 (see FIG. 15(a)), the attaching member T rests at the unset position. In such a state, as illustrated in FIG. 6(a), the proximal portions Ca and the distal portion Cb of each of the pump tubes C held by the holding portions Tb are positioned above the upper guide pins a1 and b1 of a corresponding one of the peristaltic pumps P (at an inappropriate position deviating from the appropriate position). Meanwhile, the rotor R of each of the peristaltic pumps P is stopped, with the guide pins (a1, a2, b1, and b2) (the guide portion) being in a specific phase (see FIGS. 2 and 3) and the distal portion Cb of the pump tube C being in contact with an upper part of the upper guide pin a1 (being at the inappropriate position) as illustrated by a solid chain line in FIG. 10.

In such a state, when the operating portion 5 is operated to move the anchor members 2, the attaching member T is displaced in a direction toward the predetermined position Ba, whereby the attaching member T is displaced from the unset position to the set position (see FIG. 11). When the attaching member T is displaced to the set position, as illustrated in FIG. 6(b), the proximal portions Ca of each pump tube C are moved to the appropriate position defined between the upper guide pin b1 and the lower guide pin b2. Meanwhile, the distal portion Cb of the pump tube C is at the inappropriate position on the upper part of the upper guide pin a1. Thus, an attachable state is established. In the attachable state, the distal portion Cb of the pump tube C is kept in contact with the upper part of the upper guide pin a1 (at the inappropriate position) as illustrated by a solid line in FIG. 11.

In the above attachable state, the peristaltic pump P is activated to rotate the rotor R by a predetermined angle (about 180 to 360 degrees). Then, as illustrated in FIG. 5(c), while the proximal portions Ca of the pump tube C are at the appropriate position between the upper guide pin b1 and the lower guide pin b2, the distal portion Cb of the pump tube C interferes with the upper guide pin b1 and is drawn into the stator S to the appropriate position defined between the upper guide pin a1 and the lower guide pin a2. Thus, the proximal portions Ca and the distal portion Cb of the pump tube C rest at the appropriate position, and the loading of the pump tube C onto the peristaltic pump P is complete. Such attaching work of setting the pump tube C by drawing the pump tube C to the appropriate position is referred to as loading. In such a set state, the distal portion Cb of the pump tube C is at the appropriate position defined between the upper guide pin b1 and the lower guide pin b2 as illustrated by a two-dot chain line in FIG. 11.

To detach the attaching member T, in the set state illustrated in FIG. 7(a) where the pump tube C is set in the peristaltic pump P, the operating portion 5 is operated to move the anchor members 2, whereby the attaching member T is displaced in a direction away from the predetermined position Ba. Thus, the attaching member T is displaced from the set position to the unset position (see FIG. 10). When the attaching member T is displaced to the unset position, as illustrated in FIG. 7(b), while the distal portion Cb of the pump tube C is at the appropriate position (see a two-dot chain line in FIG. 10) defined between the upper guide pin a1 and the lower guide pin a2, the proximal portions Ca of the pump tube C are moved to the inappropriate position on the upper part of the upper guide pin b1. Thus, a detachable state is established. Meanwhile, the rotor R of each of the peristaltic pumps P is stopped, with the guide pins (a1, a2, b1, and b2) (the guide portion) being in the specific phase (see FIGS. 2 and 3).

In the above detachable state, the peristaltic pump P is activated to rotate the rotor R by a predetermined angle (about 180 to 360 degrees). Then, as illustrated in FIG. 7(c), while the proximal portions Ca of the pump tube C are at the inappropriate position on the upper part of the upper guide pin a1, the distal portion Cb of the pump tube C interferes with the upper guide pin b1 and is pushed out of the stator S to the inappropriate position on the upper part of the upper guide pin b1. Thus, the proximal portions Ca and the distal portion Cb of the pump tube C rest at the inappropriate position, and the unloading of the pump tube C from the peristaltic pump P is complete. Such detaching work of unsetting the pump tube C by pushing out the pump tube C to the inappropriate position is referred to as unloading. In such an unset state, the distal portion Cb of the pump tube C is at the inappropriate position on the upper part of the upper guide pin b1 as illustrated by the solid line in FIG. 10.

The control unit 11 includes microcomputers or the like provided on the control boards K. The control unit 11 stops the rotors R with the guide pins (a1, a2, b1, and b2) (the guide portion) being in the specific phase, or rotates the rotors R by the predetermined angle, thereby executing loading or unloading. The control unit 11 may be an arbitrary combination of the following: an arithmetic device such as a CPU, a memory, a storage device, software, and an interface.

The blood purification apparatus 1 according to the present embodiment further includes detecting units 9 that detect the establishment of an attachable state or detachable state of the pump tubes C. As illustrated in FIG. 12, the detecting units 9 are each a bar-like member that is allowed to come into contact with a predetermined area defined inside a corresponding one of the holding portions Tb of the attaching member T attached to the predetermined position Ba. The detecting units 9 are urged by respective springs 9a in such a direction as to project. When the attaching member T is displaced from the unset position to the set position, the detecting units 9 follow the movement of the attaching member T and thus move against the urging force exerted by the springs 9a. The springs 9a are each incorporated such that one end thereof is in contact with a supporting frame f1 fixed to the blood purification apparatus 1, and the other end thereof is in contact with the detecting unit 9.

The detecting unit 9 is provided with a stopper 10b at the proximal end thereof. A resistor 10a is fixed to a supporting frame f2 at a position near the proximal end of the detecting unit 9. The resistor 10a and the stopper 10b form a potentiometer 10. When the detecting unit 9 is moved to move the stopper 10b, the resistor 10a converts the movement into a voltage corresponding to the length of travel or position of the stopper 10b (i.e., the length of travel or position of the detecting unit 9). Thus, the potentiometer 10 can output the voltage.

Hence, in a case where the attaching member T is to be moved from the unset position to the set position by operating the operating portion 5, if, for example, any pump tube C interferes with any elements of the peristaltic pump P and so forth and fails to be in the set position, i.e., the attachable state, a situation where the length of travel of a corresponding one of the detecting units 9 is different from a normal length of travel can be detected from the voltage outputted by the potentiometer 10. Furthermore, in the present embodiment, if any of the pump tubes C that has failed to be in the attachable state is detected by a corresponding one of the detecting units 9, one of the peristaltic pumps P that corresponds to the detected pump tube C can be identified.

Likewise, in a case where the attaching member T is to be moved from the set position to the unset position by operating the operating portion 5, if, for example, any pump tube C interferes with any elements of the peristaltic pump P and so forth and fails to be in the unset position, i.e., the detachable state, a situation where the length of travel of a corresponding one of the detecting units 9 is different from the normal length of travel can be detected from the voltage outputted by the potentiometer 10. Furthermore, in the present embodiment, if any of the pump tubes C that has failed to be in the detachable state is detected by a corresponding one of the detecting units 9, one of the peristaltic pumps P that corresponds to the detected pump tube C can be identified.

Furthermore, in the present embodiment, if any of the pump tubes C that has failed to be in the attachable state or detachable state is detected by a corresponding one of the detecting units 9 and one of the peristaltic pumps P that corresponds to the detected pump tube C is identified, the identified peristaltic pump P can be displayed on the monitor M, for example, for notification. Therefore, the operator can easily and correctly recognize the occurrence of a situation where the attachable state or detachable state is not established even after the operating portion 5 is operated.

As illustrated in FIG. 2, the detecting units 9 according to the present embodiment are each provided between adjacent two of the anchor members 2. Each detecting unit 9 is capable of detecting the establishment of the attachable state or detachable state of those pump tubes C that are to be loaded onto or unloaded from the adjacent peristaltic pumps P. That is, a single detecting unit 9 is capable of detecting a situation where either or both of the two adjacent peristaltic pumps P have failed to be in the attachable state or detachable state (in the present embodiment, the detecting unit 9 provided on the right in FIG. 2 is capable of detecting a situation where any one or all of the three adjacent peristaltic pumps P have failed to be in the attachable state or detachable state).

In the present embodiment, the length of travel (position) of the detecting unit 9 is detected by the potentiometer 10. Therefore, the situation where either (any one) of the adjacent pumps has failed to be in the attachable state or detachable state and the situation where both (all) of the adjacent pumps have failed to be in the attachable state or detachable state can be distinguished from each other in accordance with the detected length of travel or position. In such a case, which of the peristaltic pumps P has failed to be in the attachable state or detachable state can be identified more correctly. Therefore, the action to be taken after such a situation can be done more appropriately and smoothly.

As illustrated in FIG. 4, in each of the peristaltic pumps P according to the present embodiment, the rotor R provided with the rollers Ra includes a cap portion R1 and a frame portion R2. The cap portion R1 is smaller than the frame portion R2. Furthermore, the frame portion R2 has a chamfered corner R2a. Such a configuration suppresses the occurrence of a situation where the pump tube C that is being loaded or unloaded is caught on the cap portion R1 or the frame portion R2.

In the present embodiment, when the attaching member T is anchored to the predetermined position Ba of the blood purification apparatus 1 and the pump tubes C are loaded onto the respective peristaltic pumps P, a treatment apparatus for blood purification treatment is established as illustrated in FIG. 16. The treatment apparatus includes a blood circuit U including a dialyzer Q; a first dialysate introduction line L1a and a second dialysate introduction line L1b through which dialysate is introduced into the dialyzer Q; a first substitution line L2a, a second substitution line L2b, a pre-substitution line L2c, and a post-substitution line L2d through which substitution fluid is supplied to the blood circuit U; and a first drain-liquid discharge line L3a and a second drain-liquid discharge line L3b through which drain liquid is discharged from the dialyzer Q.

The blood circuit U includes an arterial blood circuit Ua and a venous blood circuit Ub. When the blood pump N is activated while a patient is punctured with the distal ends of the arterial blood circuit Ua and the venous blood circuit Ub, blood of the patient can be caused to extracorporeally circulate. The dialyzer Q has a blood introduction port Qa, a blood delivery port Qb, a dialysate introduction port Qc, and a dialysate delivery port Qd all projecting from a housing thereof. The arterial blood circuit Ua is connected to the blood introduction port Qa. The venous blood circuit Ub is connected to the blood delivery port Qb. The second dialysate introduction line L1b is connected to the dialysate introduction port Qc. The first drain-liquid discharge line L3a is connected to the dialysate delivery port Qd.

The first dialysate introduction line L1a is connected to a dialysate bag W1 that stores dialysate and is also connected to the second dialysate introduction line L1b through a temporary chamber Y. When the peristaltic pumps P provided to the first dialysate introduction line L1a and the second dialysate introduction line L1b are activated, the dialysate in the dialysate bag W1 is temporarily stored in the temporary chamber Y and is then introduced into the dialyzer Q.

The first substitution L2a is connected to a substitution-fluid bag W2 that stores substitution fluid and is also connected to the second substitution line L2b through a temporary chamber Y. The second substitution line L2b is connected to the blood circuit U through the pre-substitution line L2c connected to the arterial blood circuit Ua and through the post-substitution line L2d connected to the venous blood circuit Ub. The post-substitution line L2d is provided with a check valve V1. When the peristaltic pumps P provided to the first substitution line L2a and the second substitution line L2b are activated, the substitution fluid in the substitution-fluid bag W2 is temporarily stored in the temporary chamber Y and is then introduced into the arterial blood circuit Ua or the venous blood circuit Ub in accordance with the state of operation of the peristaltic pump P provided to the pre-substitution line L2c.

The first drain-liquid discharge line L3a is connected to the dialyzer Q and is also connected to the second drain-liquid discharge line L3b through a temporary chamber Y. The second drain-liquid discharge line L3b allows the drain liquid to be discharged therethrough to the outside of the apparatus. When the peristaltic pumps P provided to the first drain-liquid discharge line L3a and the second drain-liquid discharge line L3b are activated, the drain liquid in the dialyzer Q is temporarily stored in the temporary chamber Y and is then allowed to be discharged to the outside of the apparatus.

As described above, the pump tubes C of the attaching member T are connected to the flow routes (the first substitution line L2a, the second substitution line L2b, and the pre-substitution line L2c) through which the substitution fluid is introduced into the blood circuit U, the flow routes (the first dialysate introduction line Da and the second dialysate introduction line L1b) through which the dialysate is introduced into the dialyzer Q (a blood purifier) connected to the blood circuit U, and the flow routes (the first drain-liquid discharge line L3a and the second drain-liquid discharge line L3b) through which the drain liquid is discharged from the dialyzer Q (the blood purifier). The post-substitution line L2d may also be connected to one of the pump tubes C of the attaching member T.

In the present embodiment, none of the pump tubes C of the attaching member T is attached to the blood pump N. Alternatively, one of the pump tubes C of the attaching member T may be attached to the blood pump N by loading the pump tube C thereonto. In such a case, what is to be connected to the pump tube C of the attaching member T is the blood circuit U. That is, devices that are loadable onto the pump tubes C of the attaching member T according to the present invention include a blood purification circuit that includes the following: the blood circuit U through which the blood is caused to extracorporeally circulate; and the flow routes (the first substitution line L2a, the second substitution line L2b, and the pre-substitution line L2c (or the post-substitution line L2d)) through which the substitution fluid is introduced into the blood circuit U, the flow routes (the first dialysate introduction line L1a and the second dialysate introduction line L1b) through which the dialysate is introduced into the dialyzer Q (the blood purifier) connected to the blood circuit U, or the flow routes (the first drain-liquid discharge line L3a and the second drain-liquid discharge line L3b) through which the drain liquid is discharged from the dialyzer Q (the blood purifier).

According to the above embodiment, the attachable state in which the proximal portions Ca of the pump tube C rest at the appropriate position is established when the anchor member 2 is moved from the unset position to the set position with the guide pins (a1, a2, b1, and b2) (the guide portion) of the peristaltic pump P being stopped in the specific phase, and loading in which the guide pins (a1, a2, b1, and b2) draw the pump tube C into the stator S and rest the proximal portions Ca and the distal portion Cb of the pump tube C at the appropriate position is executed when the peristaltic pump P is activated in the attachable state such that the rotor R is rotated by the predetermined angle. Therefore, the ease of work in attaching the pump tube C to the peristaltic pump P can be increased.

The detachable state in which the proximal portions Ca of the pump tube C rest at the inappropriate position deviating from the appropriate position is established when the anchor member 2 is moved from the set position to the unset position with the guide pins (a1, a2, b1, and b2) (the guide portion) of the peristaltic pump P being stopped in the specific phase. Furthermore, unloading in which the guide pins (a1, a2, b1, and b2) push the pump tube C out of the stator S such that the proximal portions Ca and the distal portion Cb of the pump tube C rest at the inappropriate position is executed when the peristaltic pump P is activated in the detachable state such that the rotor R is rotated by the predetermined angle. Therefore, the ease of work in detaching the pump tube C from the peristaltic pump P can be increased.

The blood purification apparatus includes the control unit 11 that stops the rotor R with the guide pins (a1, a2, b1, and b2) (the guide portion) being in the specific phase and executes loading or unloading by rotating the rotor R by the predetermined angle. Therefore, the ease of work in attaching or detaching the pump tube C to or from the peristaltic pump P can be increased further.

According to the above embodiment, the peristaltic pump P is one of a plurality of peristaltic pumps P. The pump tube C is one of a plurality of pump tubes attached to the attaching member T. The number of the plurality of pump tubes C is equal to the number of the plurality of peristaltic pumps P. The plurality of pump tubes C are loaded or unloaded by moving the anchor member 2 between the set position and the unset position. Therefore, the plurality of pump tubes C can be loaded or unloaded at a time. Consequently, work hours can be reduced.

The blood purification apparatus includes the operating portion 5 with which the displacing portion 3 is operated in such a manner as to displace the attaching member T between the set position and the unset position by moving the anchor member 2. The operating portion 5 has the assisting function of assisting the exertion of the operating force. Therefore, the ease of operation of the operating portion 5 can be increased. Consequently, the movement of the anchor member 2 and the displacement of the attaching member T can be achieved smoothly. The blood purification apparatus further includes the detecting unit 9 that detects the establishment of the attachable state or detachable state of the pump tube C. Therefore, a situation where loading or unloading is not completed appropriately can be recognized.

According to the present embodiment, the pump tube C is one of a plurality of pump tubes C attached to the attaching member T. The number of the plurality of pump tubes C is equal to the number of the plurality of peristaltic pumps P. The detecting unit 9 detects any of the pump tubes C that has failed to be in the attachable state or detachable state and identifies one of the peristaltic pumps P that corresponds to the detected pump tube C. Therefore, in which of the plurality of peristaltic pumps P the situation where loading or unloading is not completed appropriately is occurring can be recognized. In particular, the detecting unit 9 according to the present embodiment detects the establishment of the attachable state or detachable state of the pump tubes C to be loaded onto or unloaded from adjacent ones of the peristaltic pumps P. Therefore, the number of detecting units 9 required can be reduced. Consequently, the manufacturing cost can be reduced.

While an embodiment has been described above, the present invention is not limited thereto. For example, a plurality of, but not seven, peristaltic pumps P or a single peristaltic pump P may be provided on the blood purification apparatus 1, and the number of pump tubes C held by the holding portions Tb may be equal to the number of peristaltic pumps P. Furthermore, while the above embodiment concerns a case where the anchor member 2 is moved by manually operating the displacing portion 3 with the operating portion 5, the anchor member 2 may be moved by operating the displacing portion 3 with an actuator such as a motor or a cylinder.

The blood purification apparatus may have other additional functions or the like, as long as an attachable state in which a first portion of a pump tube rests at an appropriate position is established when an anchor member is moved from an unset position to a set position with a guide portion of a peristaltic pump being stopped in a specific phase, and loading in which the guide portion draws the pump tube into a stator and rests the first portion and the second portion of the pump tube at an appropriate position is executed when the peristaltic pump is activated in the attachable state such that a rotor is rotated by a predetermined angle.

REFERENCE SIGN LIST

| | |
|---|---|
| 1 | blood purification apparatus |
| 2 | anchor member |
| 2a | anchor hook |
| 2b | pushing portion |
| 3 | displacing portion |
| 4 | guiding portion |
| 5 | operating portion |
| 5a | grip part |
| 5b | rocking center |
| 5c | connecting part |
| 6 | interlocking member |
| 7 | interlocking member |
| 8 | detection switch |
| 9 | detecting unit |
| 10 | potentiometer |
| 11 | control unit |
| M | monitor |
| T | attaching member |
| Ta | body |
| Tb | holding portion |
| Tc | anchoring hole |
| D | connector |
| C | pump tube |
| P | peristaltic pump |
| S | stator |
| Sa | fitting recess |
| R | rotor |
| R1 | cap portion |
| R2 | frame portion |
| Ra | roller |
| a1, a2, b1, b2 | guide pin (guide portion) |
| L | rotating shaft |
| g | positioning pin |
| h | positioning hole |
| Ba | predetermined position |

The invention claimed is:
1. A blood purification apparatus comprising:
a peristaltic pump that includes:
   a stator to which a pump tube including a first portion and a second portion is detachably attached, and
   a rotor including a roller and a guide portion, the roller delivering liquid by squeezing the pump tube attached to the stator, the guide portion retaining the pump tube at an appropriate position where the pump tube is squeezable with the roller, the rotor being rotatable about a predetermined axis;
an anchor member that anchors an attaching member to which the pump tube is attached; and
a displacing portion that displaces the attaching member between a set position and an unset position by moving the anchor member with the attaching member being anchored by the anchor member,
wherein an attachable state in which the first portion of the pump tube rests at the appropriate position is established when the anchor member is moved from the unset position to the set position with the guide portion of the peristaltic pump being stopped in a specific phase, and loading in which the guide portion draws the pump tube into the stator such that the first portion and the second portion of the pump tube rest at the appropriate position is executed when the plurality of peristaltic pump is activated in the attachable state such that the rotor is rotated by a predetermined angle;

wherein the peristaltic pump is one of a plurality of peristaltic pumps, the pump tube is one of a plurality of pump tubes attached to the attaching member, a number of the plurality of pump tubes is equal to a number of the plurality of peristaltic pumps, and the plurality of pump tubes are loaded at a time by moving the anchor member between the set position and the unset position; and wherein the plurality of peristaltic pumps circulate a liquid so that the blood purification apparatus is capable of performing a blood purification treatment.

2. A blood purification apparatus comprising:

a peristaltic pump that includes:

a rotor, the rotor including a roller and a guide portion, the roller delivering liquid by squeezing a pump tube attached to a stator, the guide portion retaining the pump tube at an appropriate position where the pump tube is squeezable with the roller;

an anchor member that anchors an attaching member to which the pump tube is attached; and a displacing portion that displaces the attaching member between a set position and an unset position by moving the anchor member with the attaching member being anchored by the anchor member, wherein a detachable state in which a first portion of the pump tube rests at an inappropriate position deviating from the appropriate position is established when the anchor member is moved from the set position to the unset position with the guide portion of the peristaltic pump being stopped in a specific phase, and unloading in which the guide portion pushes the pump tube out of the stator such that the first portion and a second portion of the pump tube rest at the inappropriate position is executed when the peristaltic pump is activated in the detachable state such that the rotor is rotated by a predetermined angle;

wherein the peristaltic pump is one of a plurality of peristaltic pumps, the pump tube is one of a plurality of pump tubes attached to the attaching member, a number of the plurality of pump tubes is equal to a number of the plurality of peristaltic pumps, and the plurality of pump tubes are unloaded at a time by moving the anchor member between the set position and the unset position; and wherein the peristaltic pump circulates a liquid so that the blood purification apparatus is capable of performing a blood purification treatment.

3. The blood purification apparatus according to claim 1, further comprising a control unit that stops the rotor with the guide portion being in the specific phase and executes unloading or the loading by rotating the rotor by the predetermined angle.

4. The blood purification apparatus according to claim 1, wherein the plurality of pump tubes are unloaded by moving the anchor member between the set position and the unset position.

5. The blood purification apparatus according to claim 1, further comprising an operating portion with which the displacing portion is operated in such a manner as to displace the attaching member between the set position and the unset position by moving the anchor member, wherein the operating portion has an assisting function of assisting exertion of an operating force.

6. The blood purification apparatus according to claim 1, further comprising a detecting unit that detects establishment of a detachable state or the attachable state of the pump tube.

7. The blood purification apparatus according to claim 6, wherein the pump tube is one of a plurality of pump tubes attached to the attaching member, a number of the plurality of pump tubes is equal to a number of the plurality of peristaltic pumps, and the detecting unit detects any of the pump tubes that has failed to be in the attachable state or the detachable state, so that the pump tubes that failed are detected pump tubes, and identifies one of the peristaltic pumps that corresponds to the detected pump tube.

8. The blood purification apparatus according to claim 7, wherein the detecting unit detects establishment of the attachable state or the detachable state of the pump tubes to be loaded onto or unloaded from adjacent ones of the peristaltic pumps.

9. The blood purification apparatus according to claim 2, further comprising a control unit that stops the rotor with the guide portion being in the specific phase and executes loading or the unloading by rotating the rotor by the predetermined angle.

10. The blood purification apparatus according to claim 2, wherein the plurality of pump tubes are loaded by moving the anchor member between the set position and the unset position.

11. The blood purification apparatus according to claim 2, further comprising an operating portion with which the displacing portion is operated in such a manner as to displace the attaching member between the set position and the unset position by moving the anchor member, wherein the operating portion has an assisting function of assisting exertion of an operating force.

12. The blood purification apparatus according to claim 2, further comprising a detecting unit that detects establishment of an attachable state or the detachable state of the pump tube.

13. The blood purification apparatus according to claim 12, wherein the peristaltic pump is a plurality of peristaltic pumps and the pump tube is one of a plurality of pump tubes attached to the attaching member, a number of the plurality of pump tubes is equal to a number of the plurality of peristaltic pumps, and the detecting unit detects any of the pump tubes that have failed to be in the attachable state or the detachable state, so that the pump tubes that failed are detected pump tubes, and identifies one of the peristaltic pumps that corresponds to the detected pump tube.

14. The blood purification apparatus according to claim 13, wherein the detecting unit detects establishment of the attachable state or the detachable state of the pump tubes to be loaded onto or unloaded from adjacent ones of the peristaltic pumps.

15. The blood purification apparatus according to claim 1, wherein the attaching member is attachable to a predetermined position of a front face of the blood purification apparatus.

16. The blood purification apparatus of claim 15, wherein the attaching member includes anchoring holes that receive a positioning pin to anchor the attaching member to the blood purification apparatus.

17. The blood purification apparatus of claim 2, wherein the attaching member is attachable to a predetermined position of a front face of the blood purification apparatus.

18. The blood purification apparatus of claim 17, wherein the attaching member includes anchoring holes that receive a positioning pin to anchor the attaching member to the blood purification apparatus.

* * * * *